US010683121B2

United States Patent
Champion et al.

(10) Patent No.: US 10,683,121 B2
(45) Date of Patent: Jun. 16, 2020

(54) METHOD FOR PREPARATION OF RESEARCH ORGANISMS

(71) Applicant: BIOSYSTEMS TECHNOLOGY LIMITED, Exeter, Devon (GB)

(72) Inventors: Olivia Champion, Exeter (GB); Richard Titball, Exeter (GB)

(73) Assignee: BIOSYSTEMS TECHNOLOGY LIMITED, Exeter, Devon (GB)

( * ) Notice: Subject to any disclaimer, the term of this patent is extended or adjusted under 35 U.S.C. 154(b) by 0 days.

(21) Appl. No.: 15/743,883

(22) PCT Filed: Aug. 17, 2016

(86) PCT No.: PCT/GB2016/052541
§ 371 (c)(1),
(2) Date: Jan. 11, 2018

(87) PCT Pub. No.: WO2017/029496
PCT Pub. Date: Feb. 23, 2017

(65) Prior Publication Data
US 2019/0084712 A1  Mar. 21, 2019

(30) Foreign Application Priority Data
Aug. 18, 2015  (GB) .................................. 1514640.0

(51) Int. Cl.
*A61L 11/00* (2006.01)
*C12N 5/00* (2006.01)
(Continued)

(52) U.S. Cl.
CPC ............ *B65B 55/18* (2013.01); *A01K 67/033* (2013.01); *A01N 1/0215* (2013.01); *A01N 31/02* (2013.01); *A61L 2/0088* (2013.01)

(58) Field of Classification Search
CPC ........... A01N 1/00; A01N 1/0215; A61L 2/00; A61L 2/0082; A61L 2/204
(Continued)

(56) References Cited

U.S. PATENT DOCUMENTS

2004/0185425 A1 *  9/2004  Okuda ..................... A01N 1/02
                                                             435/1.1

FOREIGN PATENT DOCUMENTS

AU           3222878           7/1980
CN           1300817           1/1996
(Continued)

OTHER PUBLICATIONS

International Search Report and Written Opinion of the International Searching Authority, dated Apr. 20, 2017 in corresponding international application No. PCT/GB2016/052541.
(Continued)

Primary Examiner — Monzer R Chorbaji
(74) Attorney, Agent, or Firm — Wenderoth, Lind & Ponack, L.L.P.

(57) ABSTRACT

There is provided a method or improving the surface sterility of an invertebrate organism having an external cuticle, comprising contacting an outer surface of the organism, or a portion thereof, with an aqueous alcohol solution of less than about 70% v/v for a period of less than 60 seconds. The method is especially useful to provide research-grade organisms which can be utilised in research involving injection of compositions through the external cuticle, by reducing phenotype changes resulting from introduction of surface contaminants into the interior of the organism.

18 Claims, 1 Drawing Sheet

Figure 1:
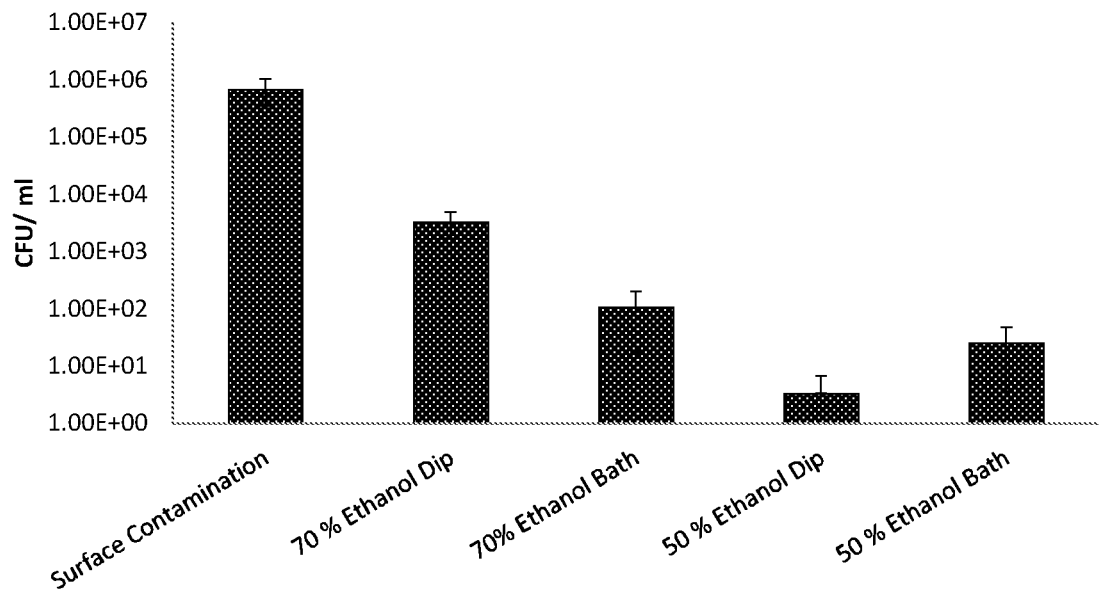

(51) Int. Cl.
*B01J 19/00* (2006.01)
*B65B 55/18* (2006.01)
*A01N 1/02* (2006.01)
*A61L 2/00* (2006.01)
*A01N 31/02* (2006.01)
*A01K 67/033* (2006.01)

(58) Field of Classification Search
USPC .......................... 422/1, 40, 34, 36; 435/325
See application file for complete search history.

(56) References Cited

FOREIGN PATENT DOCUMENTS

| | | |
|---|---|---|
| CN | 103098762 | 5/2013 |
| CN | 103977155 | 8/2014 |
| CN | 104586674 | 5/2015 |
| WO | 99/22598 | 5/1999 |

OTHER PUBLICATIONS

United Kingdom Search Report, dated Jan. 20, 2016 in corresponding GB Application No. GB1514640.0.
Shadmehr et al., "Study of Sugar Beet Cyst Nematode Life Cycle Using Plant Tissue Culture Method", Pakistan Journal of Biological Sciences, 10(17): 2910-2914 (2007).
Togashi, "A New Method for Loading *Bursaphelenchus xylophilus* (Nematoda: Aphelenchoididae) on Adult *Monochamus alternatus* (Coleoptera: Cerambycidae)", J. Ecol. Entomol. 97(3): 941-945 (2004).

\* cited by examiner

METHOD FOR PREPARATION OF RESEARCH ORGANISMS

FIELD OF THE INVENTION

The invention relates to methods for preparing invertebrate organisms suitable for laboratory research, the organisms having an external cuticle. For example, the invention relates to organisms to be used for research involving trans-dermal injection of a compound into an organism having an external cuticle.

BACKGROUND

*Galleria mellonella* (Greater Wax Moth) larvae are becoming an established disease model in biological research. The benefits of using *Galleria* are wide, ranging from the lack of ethical issues of using mammals, to the size and ease of handling, to the fact that they have a complex innate immune system like mammals (1). *Galleria* have cellular responses such as nodulisation and encapsulation, and haemolymph cells can phagocytose microbes (2, 3). It has also been found that the epithelial cells in the gut of the larvae share similar physiological phenotypes as the intestinal cells in the mammalian digestive system (3). Finally, the larvae can be incubated in temperatures up to 37° C., making it a suitable model for investigating diseases of humans.

*G. mellonella* are mainly farmed as food-stuffs for reptiles and amphibians (4) and purchased through suppliers or from local pet shops. As a consequence of the method of production, *G. mellonella* are not grown under standardised conditions and are exposed to conditions which influence the natural bacterial flora found on the larvae, which subsequently may have an effect on the susceptibility of larvae to disease (3).

The inventors have found batch-to-batch variability with *G. mellonella* larvae purchased from different suppliers. With some batches, significant numbers of larvae died in control groups dosed only with PBS (phosphate buffered saline), because the act of injecting PBS resulted in transfer of the microbial flora into the body cavity. Control group failures occur in around 30% of bait shop *G. mellonella* larvae. Similar problems are experienced with other research organisms such as *Manduca sexta* and *Caenorhabditis elegans*. This limits the potential for widespread use of these organisms as a reliable research model.

Previous workers have sterilised the alimentary tract of *Galleria mellonella* larvae by immersing the larvae in an ethyl alcohol solution for 5-6 hours (AU3222878). Although the concentration of alcohol used by these workers was not disclosed, it must have been a low concentration in order for the larvae to survive the long incubation period. The method prepares the larvae so that extracts from them can be utilised in an animal immunisation process. The method was not used to reduce the microbial flora on the cuticle of the larvae.

CN103098762 disclosed sterilising mealworms with a high concentration (75%) ethanol solution for 5-15 seconds. A mealworm treated in such a way was then packaged and kept in order to obtain a pupa and, ultimately, an adult insect. There was no suggestion that the mealworms might be useful as research-grade organisms, for use in methods requiring a reliable control group in experiments involving injection through the cuticle.

Shadmehr et al. (2007; Pakistan J. Biol. Sci. vol. 10 p 2910-2914) discussed the use of a 70% ethanol solution to sterilise cyst nematodes, for subsequent infection of plant cells. The nematodes were treated with the ethanol for 1 minute and subsequently treated with sodium hypochlorite and Triton X100. The conditions disclosed in the publication would be lethal to *Galleria mellonella* larvae.

Togashi (2004; J. Econ. Entomol. vol. 97 p 941-945) disclosed "dipping" beetle larvae into 70% and 99% ethanol. There was no indication of the time period used and there was no suggestion that the larvae might be useful as research-grade organisms, for use in methods requiring a reliable control group in experiments involving injection through the cuticle. The larvae were used as a host for nematode infection.

There remains a need to provide research-grade invertebrate organisms, especially insect larvae.

SUMMARY OF THE INVENTION

According to a first aspect of the invention, there is provided a method for improving the surface sterility of an invertebrate organism having an external cuticle, for example of an insect larva of the superorder *Endopterygota*, comprising contacting an outer surface of the organism/larva, or a portion thereof, with an aqueous alcohol solution of up to or less than about 70% v/v for a period of less than about 60 seconds.

The term "improving the surface sterility" indicates that an organism/larva which has been treated with the method according to the invention comprises fewer culturable microorganisms on its surface than prior to treatment with the method. Alternatively, the comparison may be with another organism/larva of the same species and, optionally, from the same batch or supplier, which has not been treated with the method; such an organism/larva may be termed a "control organism/larva". The improvement of surface sterility need not imply the provision of a completely sterile surface. The organism has a non-living external cuticle, i.e., an exterior surface wholly or partially formed from a protein-polysaccharide or a protein-collagen composition, for example from chitin. Since the organism is an invertebrate organism, it is not an organism such as a mammal, having a living epidermis as its external structure.

The number of culturable microorganisms on the surface of an organism/larva may be determined by any standard means known in the art, such as is described below. Briefly, the number of culturable microorganisms on the surface of an organism/larva may be determined by immersion of the organism/larva in phosphate buffered saline (PBS) solution, removing the organism/larva, plating the remaining solution or a portion and/or dilution thereof onto a Luria Broth (LB) agar plate and incubating for 24 hours at 37° C. The number of microorganism colonies which grow on the plate may then be counted. The precise details of this method of determining the number of culturable microorganisms on the surface of an organism/larva are not critical to the working of the method according to the invention. Alternative methods for determining the number of culturable microorganisms on the surface of an organism/larva may be readily devised by the skilled person.

After the organism/larva has been treated with the method according to the invention, the number of culturable microorganisms on its surface may be at least about 80%, 85%, 90%, 91%, 92%, 93%, 94%, 95%, 96%, 97%, 98% or about 99% less than prior to treatment (or in comparison to a control organism/larva as described above). The number of culturable microorganisms on its surface may be at least about 99.1%, 99.2%, 99.3%, 99.4%, 99.5%, 99.6%, 99.7%, 99.8% or at least about 99.9% less.

The number of deaths in a number (i.e., a population) of organisms obtained by the method of the invention and subsequently injected with PBS, compared with the number of deaths in an equivalent number (or population) of control organisms (i.e., an equivalent number of organisms not treated with the method) injected with PBS, may be reduced by at least 75%, for example, by at least about 80%, 81%, 82%, 83%, 84% or at least about 85%. Therefore, the method is characterised in that the number of deaths in a number of organisms obtained by the method and subsequently injected with a non-biologically active composition such as PBS, compared with the number of deaths in an equivalent number of control organisms not treated with the method and injected with the non-biologically active composition, may be reduced by at least 75%. The number of deaths may be determined, for example, within up to about 80 hours after injection, such as within about 24 hours, 36 hours, 48 hours, 60 hours or within about 72 hours.

In the method, the aqueous alcohol solution may be a methanol, ethanol or propanol (e.g., isopropanol) solution. In an embodiment, the alcohol solution may be an ethanol solution, for example a solution of ethanol prepared by mixing water such as sterile water with molecular biology-grade ethanol such as may be obtained from companies such as Sigma-Aldrich Company Ltd. (Dorset, England), by way of non-limiting example.

The aqueous alcohol solution is a solution up to or less than about 70% v/v, i.e., up to about 50%, about 55%, about 60%, about 65%, about 66%, about 67%, about 68% or up to about 69% v/v. The solution may be in the range at least about 40% v/v, up to or less than about 70% v/v. The solution may be a 40-65% v/v solution or, for example, a 40-60% v/v, 45-70% v/v, 50-70 v/v or 50-65% v/v, by way of non-limiting examples. The solution may be a solution of about 40%, 45%, 50%, 55%, 60%, 61%, 62%, 63%, 64%, 65%, 66%, 67%, 68% or about 69%. In an embodiment, the aqueous alcohol solution may be a solution of ethanol of about 50% v/v, i.e., about 45%, 46%, 47%, 48%, 49%, 50%, 51%, 52%, 53%, 54% or about 55% v/v, or in the range about 45% to about 55% v/v. The inventors have found that a solution of about 50% v/v ethanol is, surprisingly, more effective than a higher concentration solution of about 70% v/v ethanol in reducing contamination on the surface of *G. mellonella* larvae whilst avoiding larval death post-treatment, for example within up to about 80 hours after treatment has ended, such as within about 24 hours, 36 hours, 48 hours, 60 hours or within about 72 hours.

The method according to the invention may be for use with a larva which is of the order *Lepidoptera*, for example of the genus *Galleria*. In an embodiment, the larva is a *Galleria mellonella* larva. Although the method according to the invention is described in detail herein with reference to *Galleria mellonella* larvae, it will be evident to the skilled person that the method may be applicable to other insect species which undergo a larval stage, typically insects classified in the superorder *Endopterygota*, such as *Lepidoptera* insects, as mentioned above. The *Lepidoptera* insect may be selected from *G. mellonella* and *Manduca sexta*, by way of non-limiting example. Furthermore, the method may be useful with other invertebrate organisms such as worms (for example, a *Nematoda* species such as *Caenorhabditis elegans*, or a species from one of the phyla *Platyhelminthes* or *Annelida*, by way of non-limiting example), adult insects such *Drosophila melanogaster* and other organisms useful in research.

In the method, the contacting may comprise immersing the organism/larva in the aqueous alcohol solution. This may indicate placing a part or all of the external surface of the organism/larva beneath the surface of the aqueous alcohol solution and may, for example, indicate full submersion of the organism/larva under the surface so that the whole surface of the organism/larva is simultaneously contacted with the aqueous alcohol solution. During the immersing, the organism/larva may be rolled, agitated or otherwise moved within the aqueous alcohol solution, for some or all of the period during which the organism/larva is immersed.

In the method, the step of contacting the surface of the organism/larva, or a portion thereof, may extend (i.e., occur) for a period of at least about 5 seconds. This period may be continuous or may be intermittent, for example by dipping the organism/larva into and out of the aqueous alcohol solution. In such a case, the period may be measured from the time of first contact to the time of last contact between the surface of the organism and the aqueous alcohol solution. The time of last contact is the time at which the organism is removed from contact with the aqueous alcohol solution and any solution which remains on the surface of the organism after removal may be disregarded for this purpose.

The contacting may extend for a period of at least about 10, 15, 20, 25, 30, 35, 40, 45, 50 or about 55 seconds. As mentioned above, the contacting is considered to end when the organism is removed from contact with the aqueous alcohol solution; solution which remains on the surface of the organism may be disregarded for this purpose.

The particular embodiments, the aqueous alcohol solution is a solution up to or less than about 70% and the contacting may extend for about 20 seconds, for example if the aqueous alcohol solution is ethanol or methanol. In more particular embodiments, the aqueous alcohol solution may be about 40% ethanol and the contacting may extend for about 20 seconds or about 40 seconds. The aqueous alcohol solution may be about 50% ethanol and the contacting may extend for about 20 seconds or about 40 seconds or about 50 seconds. The aqueous alcohol solution may be about 60% ethanol and the contacting may extend for about 20 seconds or about 40 seconds. The aqueous alcohol solution may be about 50% methanol and the contacting may extend for about 20 seconds or about 40 seconds. The aqueous alcohol solution may be about 70% methanol and the contacting may extend for about 20 seconds. The aqueous alcohol solution may be about 50% isopropanol and the contacting may extend for about 20 seconds. The aqueous alcohol solution may be about 70% isopropanol and the contacting may extend for about 20 seconds.

At the end of the period of contacting the organism/larva with the aqueous alcohol solution, the organism/larva may be removed from the solution and optionally may be dried by applying a tissue, cloth or other absorbent material to the surface of the organism/larva, or by applying a flow of gas (such as air) to the surface of the organism/larva. An alternative or further optional step may comprise washing the organism/larva with a liquid which is not an aqueous alcohol solution, for example distilled water or phosphate-buffered saline (PBS). Other suitable liquids may also be used and the liquid may, in some circumstances, be selected in accordance with the required conditions of a subsequent experiment in which the organism/larva may be used.

A second aspect of the invention provides a method for providing a packaged research-grade invertebrate organism, such as an insect larva of the superorder *Endopterygota* (or other organism types as mentioned above), for use in research, comprising obtaining an organism/larva using the method according to the first aspect and subsequently packaging the organism/larva in a sterile environment. For example, the organism/larva may be packaged in a sterile glass or plastic container such as a box or tube, which may further contain sterile padding material such as cotton wool or fabric padding, or other material such as sterilised woodchip material. The container may be sealed with a sterile lid, bung, a film joined to the container by a heat seal, or any other routine method of closing a container. The method may comprise packaging multiple (i.e., two or more) organisms/larvae contained using the method according to the first aspect of the invention. Provision of multiple such organisms/larvae advantageously enables a user to conduct an experiment comprising at least one test and at least one control organism/larva.

A third aspect of the invention provides an invertebrate organism, such as an insect larva of the superorder *Endopterygota*, obtained by a method according to the first or second aspects of the invention. Such an organism may have a number of culturable microorganisms on its surface at least about 80%, 85%, 90%, 91%, 92%, 93%, 94%, 95%, 96%, 97%, 98% or at least about 99% less than a control organism of the same species (and, optionally, the same batch and/or supplier) which has not been obtained by a method of the invention. That is, the number of culturable microorganisms on its surface is reduced by at least this amount compared to the number prior to treatment according to the invention. The number of culturable microorganisms on its surface may be at least about 99.1%, 99.2%, 99.3%, 99.4%, 99.5%, 99.6%, 99.7%, 99.8% or at least about 99.9% less. That is, the number of culturable microorganisms on its surface is reduced by at least this amount compared to the number prior to treatment according to the invention.

The number of deaths in a number of organisms according to the third aspect of the invention injected with PBS, compared with the number of deaths in an equivalent number of control organisms injected with PBS, may be reduced by at least 75%, for example, by at least about 80%, 81%, 82%, 83%, 84% or at least about 85%. The number of deaths may be determined, for example, within up to about 80 hours after injection, such as within about 24 hours, 36 hours, 48 hours, 60 hours or within about 72 hours.

A fourth aspect of the invention provides a kit comprising more than one (or example, two or more) organism/larva according to the third aspect and packaging materials therefor. The organisms/larvae may be contained in a container of inert material such as glass or plastic, for example, a box or tube, which may further contain packaging material such as a woodchip material and/or padding material such as cotton wool or fabric padding. The container may be sealed with sealing means such as a lid, bung, a film joined to the container by a heat seal, or any other routine method of closing a container. The kit may further comprise instructions for the storage of the organisms/larvae and/or instructions for utilising the organisms/larvae in a research experiment. Provision of multiple organisms/larvae within the kit advantageously enables a user to conduct an experiment comprising at least one test and at least one control organism/larva.

A fifth aspect of the invention provides a method of testing a composition comprising injecting (i.e., inserting through an exterior surface) the composition into a first organism/larva according to the third aspect of the invention. A related aspect provides a method of testing a composition comprising obtaining a kit according to the fourth aspect of the invention, opening the packaging of said kit and injecting the composition into at least a first one of the organisms/larvae contained therein. These methods may typically further comprise a control step of injecting a non-test composition into a second organism/larva according to the third aspect of the invention or, where the kit according to the fourth aspect of the invention is utilised, at least a second one of the organisms/larvae contained therein.

For example, a method of testing a composition may comprise the steps of:
  i. obtaining a first organism/larva according to the third aspect of the invention and injecting a test composition through the cuticle of the first organism/larva into the interior of the first organism/larva;
  ii. obtaining a second organism/larva according to the third aspect of the invention and injecting a non-test composition through the cuticle of the second organism/larva into the interior of the second organism/larva;
  iii. observing the phenotype of the first and second organism/larva over a period of time, for example within up to about 80 hours after injection, such as within about 24 hours, 36 hours, 48 hours, 60 hours or within about 72 hours;
  iv. correlating differences in the phenotype of the first organism/larva compared to the phenotype of the second organism/larva with the biological activity of the test composition.

The non-test composition is a control composition having a known biological effect in the organism/larva. In some embodiments, the control composition may be one known to make no or minimal difference to the biological functions of the organism/larva. Therefore, it may be used as a baseline against which to compare a test composition, which may have one or more biological effects, to be determined by the method of testing. An example of a non-test composition routinely used in such methods is phosphate buffered saline (PBS), but other suitable non-test composition may be identified and utilised by the skilled person. For example, a non-test composition may be one which has a known biological effect to which the test composition is to be compared, to determine if the test composition has new or different biological effects compared to the non-test composition, such as reduced toxicity or increased efficacy.

In this method, where the kit according to the fourth aspect of the invention is utilised, the first and second organisms/larvae are both included within the kit.

The phenotype to be observed may be selected by the skilled person without inventive skill, according to the species of organism/larva which is being used. The phenotype may include one or more of mobility, colour and death, particularly in the case of *Galleria mellonella* larvae, for instance.

The term "composition" may indicate at least one chemical compound or a solution thereof, or a formulation comprising (by way of non-limiting example) a polynucleotide, a polypeptide, a vector comprising a polynucleotide and/or polypeptide, a vaccine, a cell and/or a mixture of any of these. The cell may be a pathogenic cell known or suspected to cause human or animal illness. The formulation may comprise any entity which it may be desirable to test for a biological function in a test organism/larva such as those described herein. Where the test composition is a solution comprising a particular entity, the non-test composition may be the solution differing only in that it lacks the entity. For example, the test composition may be a saline solution simply comprising bacterial cells, in which case the non-test composition may be an equivalent saline solution lacking the bacterial cells.

Methods for handling and injecting organisms/larvae are well known in the art and a suitable method readily may be selected by the skilled person.

Throughout the description and claims of this specification, the words "comprise" and "contain" and variations of the words, for example "comprising" and "comprises", mean "including but not limited to" and do not exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects. Generally speaking the invention extends to any novel one, or any novel combination, of the features disclosed in this specification (including the accompanying claims and drawings). Thus, features, integers or characteristics, described in conjunction with a particular aspect, embodiment or example of the invention are to be understood to be applicable to any other aspect, embodiment or example described herein, unless incompatible therewith. Moreover, unless stated otherwise, any feature disclosed herein may be replaced by an alternative feature serving the same or a similar purpose.

Figure 2:
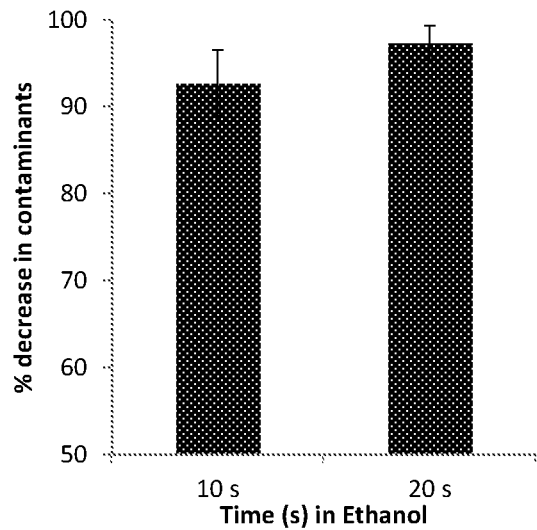

Embodiments of the invention will now be described, by way of example only, with reference to FIGS. 1 and 2 in which:

FIG. 1 shows the number of culturable microorganisms (cfu/ml, shown on a logarithmic scale) washed from the surface of G. mellonella larvae (n=10) before or after decontamination with 50% or 70% ethanol and using the "dip" or "bath" methods as described below; and FIG. 2 shows the percentage decrease in surface contaminants on G. mellonella larvae (n=10) following "bath" exposure to 50% (v/v) ethanol for different lengths of time.

EXAMPLES

In the experiments described below, the inventors have examined the level of surface contaminants on G. mellonella larvae and provide optimised decontamination assays to remove the chance of contamination and variability in infection model assays.

Materials and Methods

Final instar G. mellonella larvae were obtained from Live Foods UK and kept on woodchip at 15° C. until use. The larvae were used within two weeks of arrival. The Galleria larvae were screened for colour, weight and size before use. Larvae in a weight range between 0.2-0.3 g and light cream in colour were selected for experiments. Injections were carried out using a Hamilton syringe with 5 µl dispenser; 10 µl of inoculum was used per larva in each injection. The injection was performed into the right foreleg. Phosphate Buffer Saline (PBS, pH 7.2) was used as a control inoculum as it should not kill or harm the larvae. Absolute ethanol was diluted to the desired concentration in each assay using sterile water.

Measurement of Surface Contamination

Individual G. mellonella larva from groups of 10 were immersed thrice into 1 ml of PBS using sterilised forceps. The PBS wash was serially diluted, plated onto Luria Broth (LB) agar and incubated at 37° C. for 24 h. Any colonies of organisms visible after this period were counted. They may optionally be identified to species level, for example by use of 16S RNA sequencing.

Decontamination

Ethanol was diluted with sterile water to 70% or 50% (v/v). We tested two different decontamination techniques. Immersing the larvae (n=10 per group) thrice into a universal containing 20 ml of diluted ethanol ("dip" technique) or rolling the larvae fully submerged in a petri dish containing 20 ml of diluted ethanol ("bath" technique). To assess the microbial flora after decontamination, we used the PBS washing method outlined above.

Optimising Decontamination Time

Using the "bath" method, different lengths of time for decontamination were tested. Using sterile tweezers each larvae was rolled in 20 ml of 50% ethanol for 10 s, 20 s, 30 s or 60 s, patted dry with blue roll and dipped in sterile PBS. The PBS was plated on LB agar; plates and G. mellonella larvae were incubated at 37° C. for 24 h. The health of larvae was monitored and contaminants on the plates counted.

Survival of Decontaminated or Un-decontaminated Larvae

We injected larvae with PBS before or after decontamination. One group of G. mellonella larvae was decontaminated by rolling in 20 ml of 50% ethanol for between 10-20 s and then 10 µl PBS was injected into the right foreleg. For the second group, only 10 µl PBS was injected into the right foreleg, with no preliminary decontamination. All larvae were placed into an incubator at 37° C. for 24 h and monitored for health and survival.

Additional Alcohol Treatment Studies

Further concentrations and decontamination treatment periods were studied. In each case, ten Galleria larvae were used, placed into a sterile mesh tray and immersed using the "dip" method into isopropyl alcohol, methanol or ethanol, prepared to varying concentrations by dilution with sterile water as described above. The treatment conditions were:

| Isopropyl alcohol | 50% and 70%: 20 second and 40 seconds |
| Methanol | 50% and 70%: 20 seconds and 40 seconds |
| Ethanol | 40% and 60%: 20 seconds and 40 seconds |
| Ethanol | 50%: 20 seconds, 40 seconds and 50 seconds |

Larvae were patted dry on paper towel and grasped with sterile forceps dip larvae individually into PBS three times, for measurement of surface contamination as described above.

Results

Decontamination using 50% or 70% Ethanol

In our initial studies we found a microbial flora of up to $10^5$ culturable cells on the surface of G. mellonella larvae (FIG. 1). We tested two methods for surface decontamination by immersing the larvae briefly three times in ethanol ("dip" technique) or rolling the larvae briefly three times in a bath of ethanol ("bath" technique). It can be seen that 50% (v/v) ethanol provided better decontamination than 70% (v/v) ethanol. The Figure shows a percentage reduction in surface contaminants compared to control of 99.52% for the 70% ethanol dip, 99.98% reduction for the 70% ethanol bath and 99.99% reduction for the 50% ethanol dip and bath.

Therefore, whilst the bath method was more effective when using 70% ethanol, there was no significant difference in the degree of decontamination using the dip or bath method with 50% ethanol. For reasons of ease of use, the bath method was selected this method for the next experiments.

Toxicity of Ethanol Towards G. Mellonella Larvae

We next determined whether bath immersion in 50% (v/v) ethanol for the times shown was toxic to the G. mellonella larvae (n=10). The results showed no evidence of toxicity after a single 10, 20 or 30 s exposure to ethanol, but the change in pigmentation of larvae exposed to ethanol for 60 s, suggested that these larvae had mounted a response to a physiological stress. We selected 10 and 20 s of decontamination by bath immersion with 50% ethanol for our subsequent studies.

TABLE 1

Effect of 50% (v/v) ethanol on G. mellonella larvae. Galleria were incubated at 37° C. and recorded at 24 h and 48 h post decontamination

| Length of Exposure (secs) | Observations at 24 h | Observations at 48 h |
|---|---|---|
| 10 | No death or pigment change | No death or pigment change |
| 20 | No death or pigment change | No death or pigment change |
| 30 | No death or pigment change | No death or pigment change |
| 60 | No death BUT there was a pigment change | 15% death |

Optimisation of Decontamination Time

We next determined whether decontamination was equally efficient after a single 10 or 20 s exposure to 50% (v/v) ethanol. Groups of 10 larvae were bath decontaminated in 50% (v/v) ethanol. Our results showed similar levels of decontamination after exposure for either 10 or 20 s. The larvae were then washed with PBS to release microorganisms on their surface and the PBS wash diluted and plated out. FIG. 2 shows the percentage decrease of surface contaminants for larvae rolled in 20 ml ethanol for the time shown, compared to the surface contaminants (shown in FIG. 1) for control larvae not exposed to ethanol.

Effect of Decontamination on Survival of Control Group Larvae

Finally, we investigated whether decontamination of the larvae improved the survival of larvae which were subsequently injected with PBS. Groups of 10 larvae were bath decontaminated with a single 20s bath exposure to 50% (v/v) ethanol. These larvae were dried and then injected 10 µl PBS into the right foreleg. The larvae were placed at 37° C. and survival recorded over the next 24 hours.

We saw 100% survival of 19/20 groups which had been surface decontaminated with ethanol. In contrast, only 14/20 groups of the un-decontaminated larvae showed 100% survival. This represents a reduction in deaths of 83%.

Decontamination Using Alternative Aqueous Alcohol Solutions for Different Time Periods Table 2 shows the results of varying the immersion period and the type of alcohol on the decontamination of the surface of the larvae and their subsequent survival:

TABLE 2

Reduction in microbial surface contamination of larvae and larval survival following decontamination

| Treatment | 24 hrs | 48 hrs | 72 hrs | % reduction in microbial surface contamination |
|---|---|---|---|---|
| Control (PBS) | 10/10 | 10/10 | 10/10 | 0 |
| Ethanol | | | | |
| 40% | | | | |
| 20 s | 10/10 | 10/10 | 10/10 | 95.7 |
| 40 s | 10/10 | 10/10 | 10/10 | 99.2 |
| 50% | | | | |
| 20 s | 10/10 | 10/10 | 10/10 | 99.0 |
| 40 s | 10/10 | 10/10 | 10/10 | 98.9 |
| 50 s | 10/10 | 10/10 | 10/10 | 99.4 |
| 60% | | | | |
| 20 s | 10/10 | 8/10 | 7/10 | 98.4 |
| 40 s | 10/10 | 9/10 | 8/10 | 99.1 |
| Methanol | | | | |
| 50% | | | | |
| 20 s | 9/10 | 9/10 | 9/10 | 99.0 |
| 40 s | 10/10 | 10/10 | 10/10 | 99.7 |
| 70% | | | | |
| 20 s | 10/10 | 10/10 | 10/10 | 99.9 |
| 40 s | 9/10 | 9/10 | 9/10 | 99.9 |
| Isopropyl alcohol | | | | |
| 50% | | | | |
| 20 s | 10/10 | 10/10 | 10/10 | 99.9 |
| 40 s | 9/10 | 9/10 | 9/10 | 99.9 |
| 70% | | | | |
| 20 s | 10/10 | 10/10 | 10/10 | 99.9 |
| 40 s | 9/10 | 9/10 | 9/10 | 99.8 |

Discussion

The results from our initial experiments show that a large microbial flora is carried on the surface of a G. mellonella larva. The contaminants were not identified at the species level in this study, but visual analysis of the plates revealed a likely combination of bacteria, yeast and fungi. These contaminants can be introduced into the larva haemolymph through the injection point when challenging larvae. We believe that the deaths we have seen in past experiments in control groups challenged with PBS was a consequence of the introduction of this microbial flora into the body cavity of the larvae. Deaths in control groups can make the interpretation of results from test groups difficult. Therefore, the plan in this study was to identify a way of surface decontaminating the larvae, so that deaths in control groups were avoided, and therefore improving the quality of the data obtained from experiments using G. mellonella larvae. Galleria larvae are scored as dead when there is no movement when gently probed with a pipette tip. Colour is also an indicator of a response to infection or injury as such larvae produce melanin which creates a colour change of cream to pale or dark brown (4).

In summary, we report a method that significantly reduces the surface microbial flora on larvae without apparently affecting the health of the larvae. This method involves rolling the larvae for 20 s in a bath of ethanol followed by allowing them to dry. We selected the bath method for some decontamination experiments because there was no significant difference in the degree of decontamination using 50% ethanol with the dip or bath method. In the initial studies, we demonstrated that decontaminating the surface of the larvae reduced bacterial contaminants of by between 97% and 99.99%. This surface decontamination of larvae significantly improved the survival of larvae dosed by injection with PBS, reducing deaths in such control groups by 83%.

The additional data shown in Table 2 establishes a preferred concentration when ethanol, methanol or isopropanol is used of up to about 70%, ideally in the range 40-60% v/v, for use for an immersion period of approximately 20 seconds. Longer treatment conditions can be tolerated without larval death when an ethanol or methanol concentration of up to about 50% v/v is used.

These results indicate that it will now be possible to have control groups of *G. mellonella* larvae where none of the larvae die. This finding has two important implications. First, the statistical power of experiments will be increased by including reliable control groups where none of the larvae die. Secondly, *G. mellonella* larvae are often used to study microbial pathogens of humans or chemical toxicity. Our method will reduce the possibility that some of the disease seen after dosing with the pathogen of interest is actually a consequence of transfer of the microbial flora on the larval surface into the body cavity. This will provide more reliable results and enable the more widespread use of this experimental model, reducing the need for use of animal-based experimentation.

REFERENCES

1. Ramarao N, Nielsen-Leroux C, Lereclus D. The Insect *Galleria mellonella* as a Powerful Infection Model to Investigate Bacterial Pathogenesis. Journal of Visualized Experiments : JoVE. 2012(70):4392.
2. Cook S M, McArthur J D. Developing *Galleria mellonella* as a model host for human pathogens. Virulence. 2013;4(5):350-3.
3. Nathan S. New to *Galleria mellonella*: Modeling an ExPEC infection. Virulence. 2014;5(3):371-4.
4. Champion O L, Karlyshev A V, Senior N J, Woodward M, La Ragione R, Howard S L, et al. Insect infection model for Campylobacter jejuni reveals that O-methyl phosphoramidate has insecticidal activity. The Journal of infectious diseases. 2010;201(5):776-82.
5. Mylonakis E, Moreno R, El Khoury J B, Idnurm A, Heitman J, Calderwood S B, et al. *Galleria mellonella* as a model system to study *Cryptococcus neoformans* pathogenesis. Infection and immunity. 2005;73(7):3842-50.
6. Aperis G, Fuchs B B, Anderson C A, Warner J E, Calderwood S B, Mylonakis E. *Galleria mellonella* as a model host to study infection by the *Francisella tularensis* live vaccine strain. Microbes and infection/Institut Pasteur. 2007;9(6):729-34.
7. Harrison F, Browning L E, Vos M, Buckling A. Cooperation and virulence in acute *Pseudomonas aeruginosa* infections. BMC biology. 2006;4:21.
8. Garcia-Rodas R, Casadevall A, Rodriguez-Tudela J L, Cuenca-Estrella M, Zaragoza O. *Cryptococcus neoformans* capsular enlargement and cellular gigantism during *Galleria mellonella* infection. PloS one. 2011;6(9):e24485.
9. Navarro-Velasco G Y, Prados-Rosales R C, Ortiz-Urquiza A, Quesada-Moraga E, Di Pietro A. *Galleria mellonella* as model host for the trans-kingdom pathogen *Fusarium oxysporum*. Fungal genetics and biology : FG & B. 2011;48(12):1124-9.
10. Walsh K T, Webster J M. Interaction of microbial populations in Steinernema (Steinernematidae, Nematoda) infected *Galleria mellonella* larvae. Journal of invertebrate pathology. 2003;83(2):118-26.
11. Beeton M L, Alves D R, Enright M C, Jenkins A T. Assessing phage therapy against *Pseudomonas aeruginosa* using a *Galleria mellonella* infection model. International journal of antimicrobial agents. 2015;46(2):196-200.

The invention claimed is:

1. A method for improving the surface sterility of a living invertebrate research organism of the order *Lepidoptera* having an external cuticle, comprising contacting an outer surface of the organism, or a portion thereof, with an aqueous alcohol solution of up to about 70% v/v for a period of less than about 60 seconds, wherein the survival rate of the surface sterilised research organism when injected is improved relative to controls.

2. The method according to claim 1 wherein the aqueous alcohol solution is a 40-65% v/v solution.

3. The method according to claim 1 wherein the alcohol is ethanol, methanol or isopropanol.

4. The method according to claim 1 wherein the aqueous alcohol solution is a 40-60% v/v ethanol solution.

5. The method according to claim 1 wherein the aqueous alcohol solution is an about 50% v/v ethanol solution.

6. The method according to claim 1 wherein the organism is one or more insect larva selected from the group consisting of a larva of the genus *Galleria*, and a *Galleria mellonella* larva.

7. The method according to claim 1 wherein the contacting comprises immersing the organism in the aqueous alcohol solution.

8. The method according to claim 7 wherein the immersing comprises rolling, agitating or otherwise moving the organism in the aqueous alcohol solution.

9. The method according to claim 1 wherein the contacting extends for a period of time selected from the group consisting of at least 5 seconds, at least 10 seconds, about 20 seconds, about 30 seconds, and about 40 seconds.

10. A method for providing a living packaged invertebrate organism having an external cuticle, comprising obtaining an invertebrate organism having an external cuticle and subsequently packaging the organism in a sterile environment, wherein the organism obtained has been subjected to a method for improving surface sterility, said method comprising contacting an outer surface of the organism, or a portion thereof, with an aqueous alcohol solution of up to about 70% v/v for a period of less than about 60 seconds.

11. The method according to claim 10 wherein the organism is an insect larva of the superorder Endopterygota.

12. A kit comprising (i) a population of living invertebrate organisms of the order *Lepidoptera* having an external cuticle, wherein the organisms have been subjected to a method for improving surface sterility, said method comprising contacting an outer surface of the organisms, or a portion thereof, with an aqueous alcohol solution of up to about 70% v/v for a period of less than about 60 seconds; and (ii) sterile packaging materials.

13. A method of testing a composition comprising injecting a test composition into at least one member of a population of living invertebrate organisms of the order *Lepidoptera* having an external cuticle, wherein the organisms have been subjected to a method for improving surface sterility, said method comprising contacting an outer surface of the organisms, or a portion thereof, with an aqueous alcohol solution of up to about 70% v/v for a period of less than about 60 seconds.

14. The method according to claim 13 further comprising a control step of injecting a non-test composition into at least one member of the population that has not received the test composition.

15. A method according to claim 13 wherein the invertebrate organism is a *Galleria mellonella* larva.

16. A method of testing a composition comprising:
(a) Obtaining a kit comprising (i) a population of living invertebrate organisms of the order *Lepidoptera* having an external cuticle wherein the organisms have been subjected to a method for improving surface sterility, said method comprising contacting an outer surface of the organisms, or a portion thereof, with an aqueous alcohol solution of up to about 70% v/v for a period of less than about 60 seconds; and (ii) sterile packaging materials,
(b) Opening the package of said kit, and
(c) Injecting the composition into at least one member of the population of invertebrate organisms.

17. A method according to claim 16 further comprising a control step of injecting a non-test composition into at least one member of the population that has not received the test composition.

18. A method of testing a composition comprising the steps of:
i. obtaining a first member of a population of living invertebrate organisms/larva of the order *Lepidoptera* having an external cuticle, wherein the population has been subjected to a method for improving surface sterility, said method comprising contacting an outer surface of the organisms/larva, or a portion thereof, with an aqueous alcohol solution of up to about 70% v/v for a period of less than about 60 seconds and injecting a test composition through the cuticle of the first member into the interior of the first organism/larva;
ii. obtaining a second member of the population and injecting a non-test composition through the cuticle of the second member into the interior of the second member;
iii. observing the phenotype of the first and second members of the population over a period of time;
iv. correlating differences in the phenotype of the first member compared to the phenotype of the second member with the biological activity of the test composition.

* * * * *